(12) United States Patent
Suzuki et al.

(10) Patent No.: US 6,443,933 B1
(45) Date of Patent: Sep. 3, 2002

(54) DISPOSABLE BODY WASTES ABSORBENT ARTICLE

(75) Inventors: Naomi Suzuki; Yoshitaka Mishima, both of Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 09/570,359

(22) Filed: May 12, 2000

(30) Foreign Application Priority Data

May 12, 1999 (JP) .......................................... 11-131515

(51) Int. Cl.⁷ ................................................ A61F 13/15
(52) U.S. Cl. ......................... 604/385.04; 604/385.14; 604/305.23; 604/385.02; 604/385.01; 604/358; 604/378; 604/387; 604/383
(58) Field of Search ...................... 604/385.14, 385.04, 604/385.23

(56) References Cited

U.S. PATENT DOCUMENTS

| | | | | |
|---|---|---|---|---|
| 3,709,221 A | * | 1/1973 | Riely | .......................... 128/156 |
| 4,623,342 A | | 11/1986 | Ito et al. | |
| 5,542,941 A | | 8/1996 | Morita | |
| 5,851,204 A | * | 12/1998 | Mizutani | ............... 604/385.02 |
| 5,968,029 A | * | 10/1999 | Chappell | ............... 604/385.01 |

FOREIGN PATENT DOCUMENTS

| | | |
|---|---|---|
| EP | 0 604 764 A1 | 7/1994 |
| EP | 0 681 820 A2 | 11/1995 |
| EP | 1 040 810 A2 | 10/2000 |

* cited by examiner

Primary Examiner—Rodney M. Lindsey
Assistant Examiner—Angela J Grayson
(74) Attorney, Agent, or Firm—Baker & Daniels

(57) ABSTRACT

A disposable body wastes absorbent article including a pair of barrier side flaps and a pair of barrier end flaps, each of these flaps having a lower portion folded in a sidewise U-shape such that an open end of the U-shape is opposed to an upper portion of the flap.

10 Claims, 5 Drawing Sheets

DISPOSABLE BODY WASTES ABSORBENT ARTICLE

BACKGROUND OF THE INVENTION

This invention relates to a disposable body wastes absorbent article such as a urine pad, an incontinence pad, a menstruation napkin and the like.

Japanese Patent Application Disclosure No. 1994-178795 describes an absorbent article basically comprising a diaper cover and a rectangular insertion pad. The diaper cover has a longitudinally front and rear waist regions and a crotch region extending between these two waist regions and is provided along its transversely opposite side edges with a pair of holding flaps biased to rise on the cover. The insertion pad is made of an absorbent material and laid between the holding flaps on the upper side of the cover. The pad comprises an absorbent core and a water-pervious sheet covering the core.

Japanese Patent Application Disclosure No. 1996-289902 describes a disposable diaper comprising a liquid-pervious topsheet consisting of a central sheet and side sheets provided separately of the central sheet, a liquid-impervious backsheet and a liquid-absorbent core disposed between the topsheet and the backsheet wherein the pair of side sheets define a pair of barrier flaps longitudinally extending in the outer vicinity of transversely opposite side edges of the core and being biased to rise on the backsheet. Each of the side sheets comprises a proximal portion extending longitudinally of the diaper, an inner side portion extending transversely inward from the proximal portion and provided with an elastic member bonded with under tension, and an outer side portion extending transversely outward from the proximal portion. The side sheets overlapping the portions of the backsheet extending transversely outward from transversely opposite side edges of the central sheet have their inner surfaces along the respective proximal portions and outer side portions fixed to the upper surface of the backsheet. Longitudinally front and rear ends of the respective side sheets are collapsed inwardly of the diaper and have their inner surfaces fixed to the upper surface of the topsheet.

SUMMARY OF THE INVENTION

It is an object of this invention to provide a disposable absorbent article having side flaps that can be smoothly risen to prevent leakage of body wastes from otherwise occurring beyond peripheries of the article.

According to this invention, there is provided a disposable body wastes absorbent article having transversely opposite side edges and longitudinally opposite ends, comprising a laminated panel comprising a liquid-pervious topsheet, a liquid-impervious backsheet and a liquid-absorbent core disposed therebetween; wherein:

the panel is provided along the transversely opposite side edges with a pair of barrier side flaps extending longitudinally of the panel and being biased to rise on an upper surface of the panel and along the longitudinally opposite ends with a pair of barrier end flaps extending transversely of the panel;

each of the barrier side flaps comprises a first side section extending on an upper side of the panel longitudinally thereof, a second side section extending on a lower side of the panel longitudinally thereof and longitudinally opposite ends overlying the longitudinally opposite ends of the panel on the upper side thereof, the second side section being folded in a sidewise U-shape in a cross section thereof along a folding line extending longitudinally of the panel with an open end of the sidewise U-shape opposed to the first side section and with an inner surface of the second side section put flat together so as to define a free side subsection and a fixed side subsection placed on the free side subsection and the fixed side subsection having an upper surface thereof fixed to the lower surface of the panel along the transversely opposite side edges of the panel;

each of said barrier end flaps comprises a first end section extending on the upper surface of the panel transversely thereof, a second end section extending on the lower surface of the panel transversely thereof and transversely opposite ends overlying the longitudinally opposite ends of the panel on an upper side thereof, the second end section being folded in a sidewise U-shape in a cross section thereof along a folding line extending transversely of the panel with an open end of the U-shape opposed to the first end section and with an inner surface of the second end section put flat together so as to define a free end subsection and a fixed end subsection placed on the free end subsection and the fixed end subsection having an upper surface thereof fixed to the lower surface of the panel along the longitudinally opposite ends of the panel; and the longitudinally opposite ends of the barrier side flap are collapsed inward transversely of the panel while the transversely opposite ends of the barrier end flap are collapsed inward longitudinally of the panel to place the longitudinally opposite ends of the barrier side flap and the transversely opposite ends of the barrier end flap upon each other and the longitudinally opposite ends of the barrier side flap are fixed to the transversely opposite ends of the barrier end flap.

DETAILED DESCRIPTION OF THE PREFERRED EMBODIMENTS

Details of a disposable body wastes absorbent article according to this invention will be more fully understood from the description of an absorbent pad attached to an inner surface of a diaper cover as one embodiment given hereunder with reference to the accompanying drawings.

Figure 1:
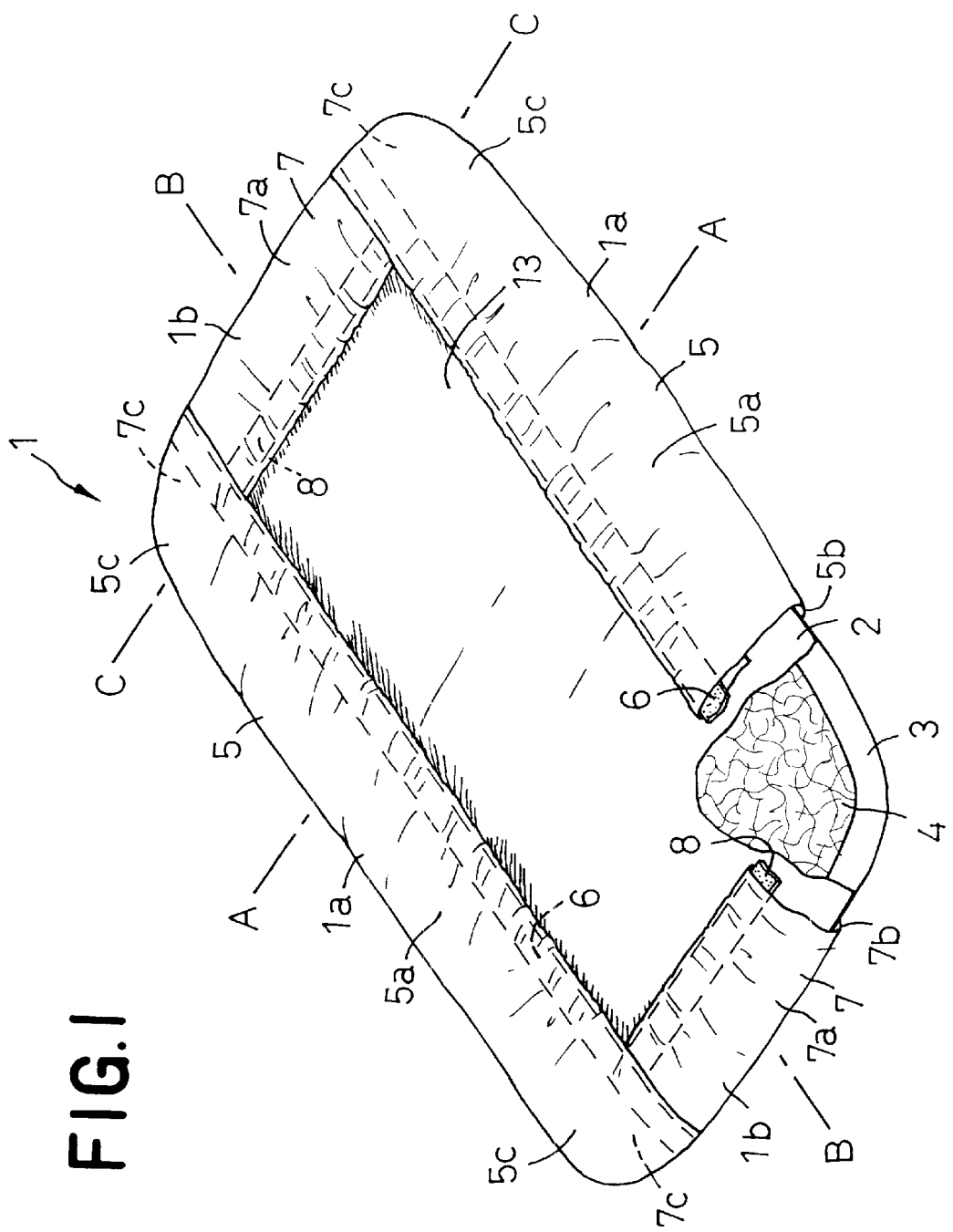
FIG. 1 is a partially cutaway perspective view showing an article according to this invention.

FIG. 1 is a partially cutaway perspective view showing a pad formed by a laminated panel 1. The panel 1 comprises a liquid-pervious topsheet 2, a liquid-impervious backsheet 3 and a liquid-absorbent core 4 disposed between these two sheets 2, 3 and joined to the inner surface of at least one of the two sheets 2, 3. The panel 1 has transversely opposite side edges 1a extending longitudinally of the panel 1 and longitudinally opposite ends 1b extending transversely of the panel 1.

Along the side edges 1a of the panel 1, a pair of barrier side flaps 5 extend longitudinally of the panel 1. The panel 1 is provided along the longitudinally opposite ends 1*b* with a pair of barrier end flaps 7 to which film-like elastic members 8 are secured under tension. The panel 1 has an opening 13 surrounded by the barrier side flaps 5 and the barrier end flaps 7 so that the topsheet 2 may be exposed in the opening 13.

Each of the barrier side flaps 5 is formed by a nonwoven fabric and comprises an upper side section 5*a* longitudinally extending on the upper side of the panel 1 between the longitudinally opposite ends 1*b* of the panel 1 and fixed neither to the topsheet 2 nor to the backsheet 3, a lower side section 5*b* longitudinally extending on the lower side of the panel 1, and longitudinally opposite ends 5*c* overlying the longitudinally opposite ends 1*a* of the panel 1.

Each of the barrier end flaps 7 is formed by a nonwoven fabric and comprises an upper end section 7*a* transversely extending on the upper side of the panel 1 between the transversely opposite side edges 1*a* of the panel 1 and fixed neither to the topsheet 2 nor the backsheet 3, a lower end section 7*b* transversely extending on the lower side of the panel 1, and transversely opposite ends 7*c* overlying transversely opposite ends of the respective longitudinally opposite ends 1*b* of the panel 1. Flexible side flaps 1*a*1 and end flaps 1*b*1 are formed by portions of the topsheet 2 and the backsheet 3 extending outward from side edges and end edges of the core 4, respectively.

Figure 2:
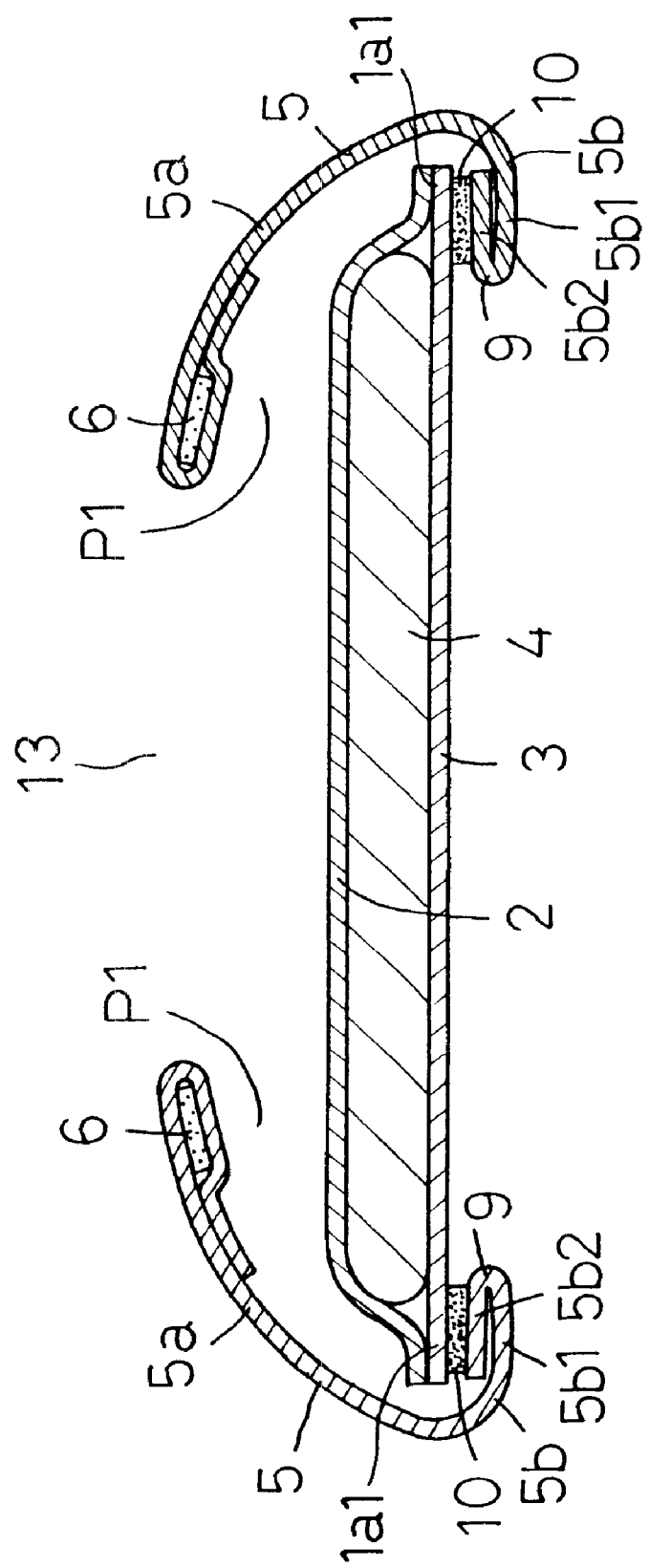
FIG. 2 is a fragmentary sectional view taken along line A—A in FIG. 1.

FIG. 2 is a sectional view taken along line A—A in FIG. 1. The lower side section 5*b* of the barrier side flap 5 has a folding line 9 extending longitudinally of the panel 1 and positioning inside the lower side section 5*b*, along which the lower side section 5*b* is folded in a sidewise U-shape in a cross section thereof with its inner surface put flat together. The lower side section 5*b* comprises a free subsection 5*b*1 transversely extending from the associated side edge 1*a* of the panel 1 with a predetermined width and a fixed subsection 5*b*2 extending from the folding line 9 transversely outward of the panel 1 with a predetermined width. The surface of the fixed subsection 5*b*2 opposed to the side flap 1*a*1 is fixed to the lower surface of the side flap 1*a*1 by means of adhesive agent 10. The upper side section 5*a* is folded back inwardly of the panel 1 so as to wrap the elastic member 6 which is secured to the side section 5*a* under tension. under resilience of the barrier side flap 5, the free subsection 5*b*1 are biased along the folding line 9 so as to restore their positions at which they occupied before the lower side section 5*b* has been folded along the folding line 9. Under such a biasing effect, the upper side section 5*a* moves away from the upper surface of the panel 1 and this movement facilitates the barrier side flap 5 to rise on the upper surface of the panel 1. With the panel 1 being curved longitudinally with its inner surface inside when the panel 1 is worn, the elastic member 6 contracts to rise the barrier side flap 5 and consequently the upper side section 5*a* of the barrier side flap 5 cooperates with the topsheet 2 to form a pocket P1 opening inwardly of the panel 1.

The free subsection 5*b*1 is fixed neither to the side flap 1*a*1 nor to the fixed subsection 5*b*2 and therefore a height by which the barrier side flap 5 can rise when a side edge region of the panel 1, particularly the side flap 1*a*1 is bent, with the panel 1 is worn, is substantially equal to a length of the upper side section 5*a* plus a length of the free subsection 5*b*1 as measured transversely of the panel 1. Accordingly, even if the panel 1 is spaced from a wearer's skin by the length of the upper side section 5*a* when the panel 1 is worn, the length of the free subsection 5*b*1 can compensate this and thereby maintain a good fit of the barrier side flap 5 around the wearer's leg.

Figure 3:
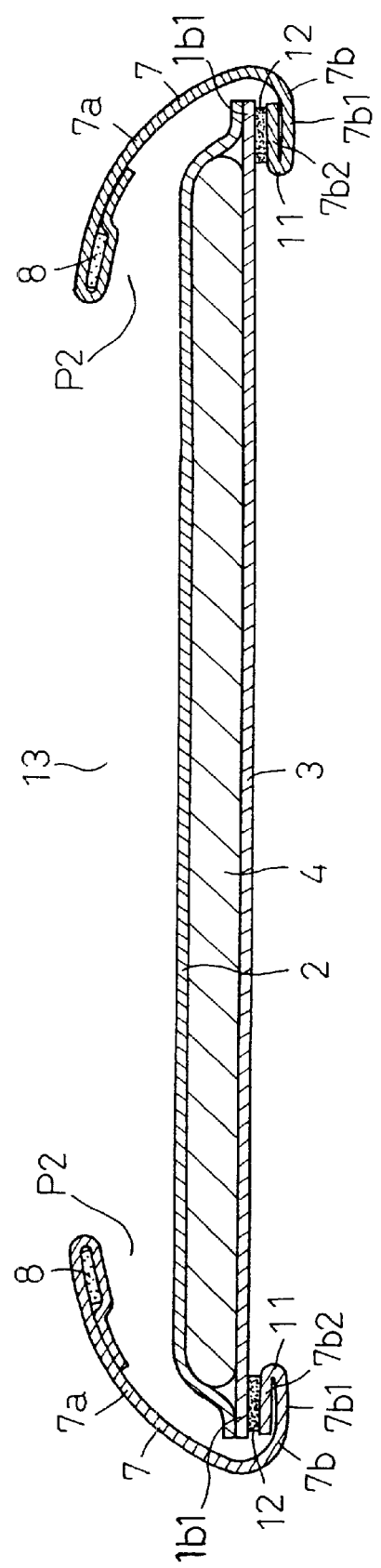
FIG. 3 is a fragmentary sectional view taken along line B—B in FIG. 1.
Figure 4:
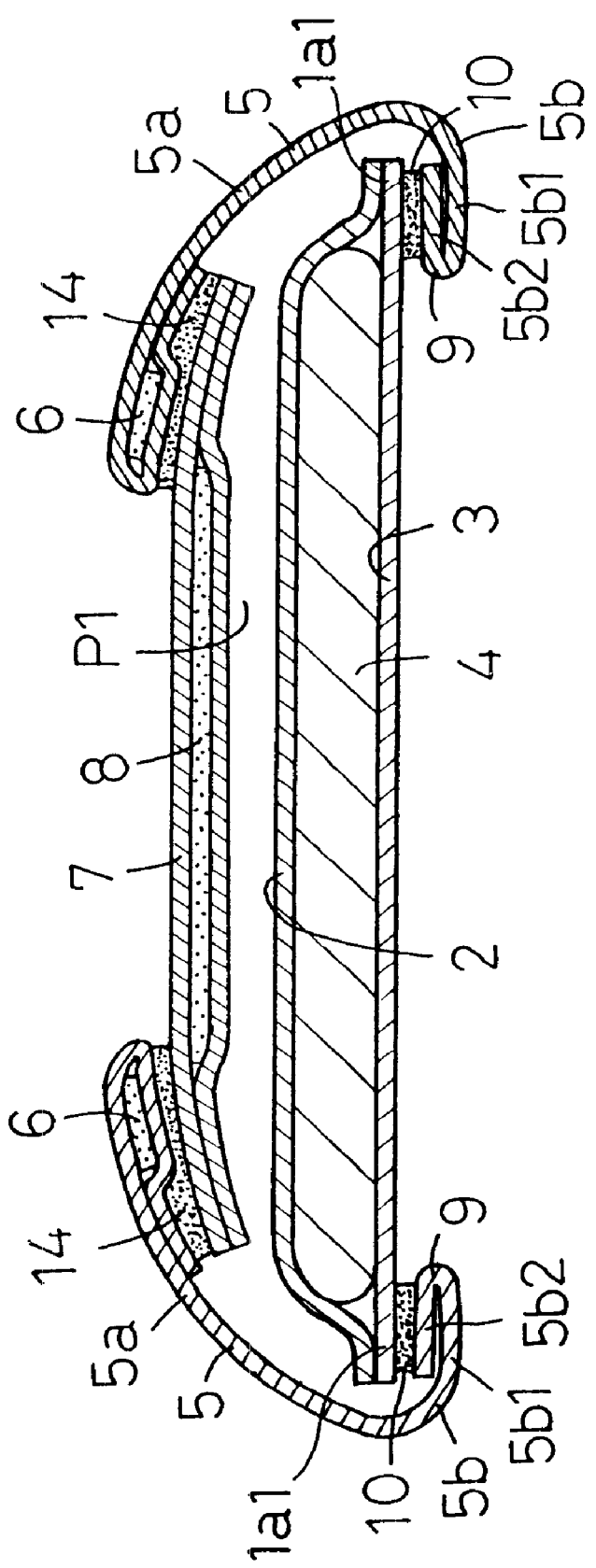
FIG. 4 is a fragmentary sectional view taken along line C—C in FIG. 1.

FIGS. 3 and 4 are fragmentary sectional views taken along lines B—B and C—C in FIG. 1, respectively. The lower end section 7*b* of the barrier end flap 7 has a folding line 11 extending transversely of the panel 1 and positioning inside the lower end section 7*b*, along which the lower end section 7*b* is folded in a sidewise U-shape in a cross section thereof with its inner surface put flat together. The lower end section 7*b* comprises a free subsection 7*b*1 longitudinally extending inward from the end 1*b* of the panel 1 and a fixed subsection 7*b*2 longitudinally extending outward from the folding line 11. The surface of the fixed subsection 7*b*2 opposed to the end flap 1*b*1 is fixed to the lower surface of the end flap 1*b*1 by means of adhesive agent 12. The upper end section 7*a* is folded back inwardly of the panel 1 so as to wrap the elastic member 8 which is secured to the upper end section 7*a* under tension.

The barrier side flap 5 and the barrier end flap 7 are arranged in a positional relationship to each other as illustrated. Specifically, the longitudinally opposite ends 5*c* of the barrier side flap 5 are collapsed inward transversely of the panel 1 and the transversely opposite ends 7*c* of the barrier end flap 7 are collapsed inward longitudinally of the panel 1 to place the longitudinally opposite ends 5*c* of the barrier side flap 5 and the transversely opposite ends 7*c* of the barrier end flap 7 upon each other. In such a positional relationship between the barrier side flap 5 and the barrier end flap 7, lower surfaces of the transversely opposite ends 5*c* are fixed to upper surfaces of the transversely opposite ends 7*c*, respectively. It is also possible to fix the upper surfaces of the longitudinally opposite ends 5*c* to the lower surfaces of the transversely opposite ends 7*c*.

Under resilience of the barrier end flap 7, the free subsection 7*b*1 are biased along the folding line 11 so as to restore their positions before the lower end section 7*b* has been folded along the folding line 11. Under such a biasing effect, the upper end section 7*a* moves away from the upper surface of the panel 1 and this movement facilitates the barrier end flap 7 to rise on the upper surface of the panel 1. Contraction of the elastic member 8 causes the barrier end flap 7 to rise on the panel 1 and consequently the upper end section 7*a* of the barrier end flap 7 cooperates with the topsheet 2 to form a pocket P2 opening inwardly of the panel 1.

The free subsection 7*b*1 is fixed neither to the end flap 1*b*1 nor to the fixed subsection 7*b*2 and therefore a height by which the barrier end flap 7 can rise when a end edge region of the panel 1, particularly the end flap 1*b*1 is bent, with the panel 1 worn, is substantially equal to a length of the upper end section 7*a* plus a length of the free subsection 7*b*1 as measured transversely of the panel 1. Accordingly, even if the panel 1 is spaced from a wearer's skin by the length of the upper end section 7*a* when the panel 1 is worn, the length of the free subsection 7*b*1 can compensate this and thereby maintain a good fit of the barrier end flap 7 around the wearer's skin.

For the panel 1, the upper side sections 5*a* of the barrier side flap 5 cooperate with the upper end sections 7*a* of the barrier end flap 7 to function as barriers while the pockets P1, P2 function to hold excretion exuding from the core 4. In this manner, the panel 1 can prevent excretion from leaking beyond the transversely opposite side edges 1*a* as well as beyond longitudinally opposite ends 1*b*.

Figure 5:
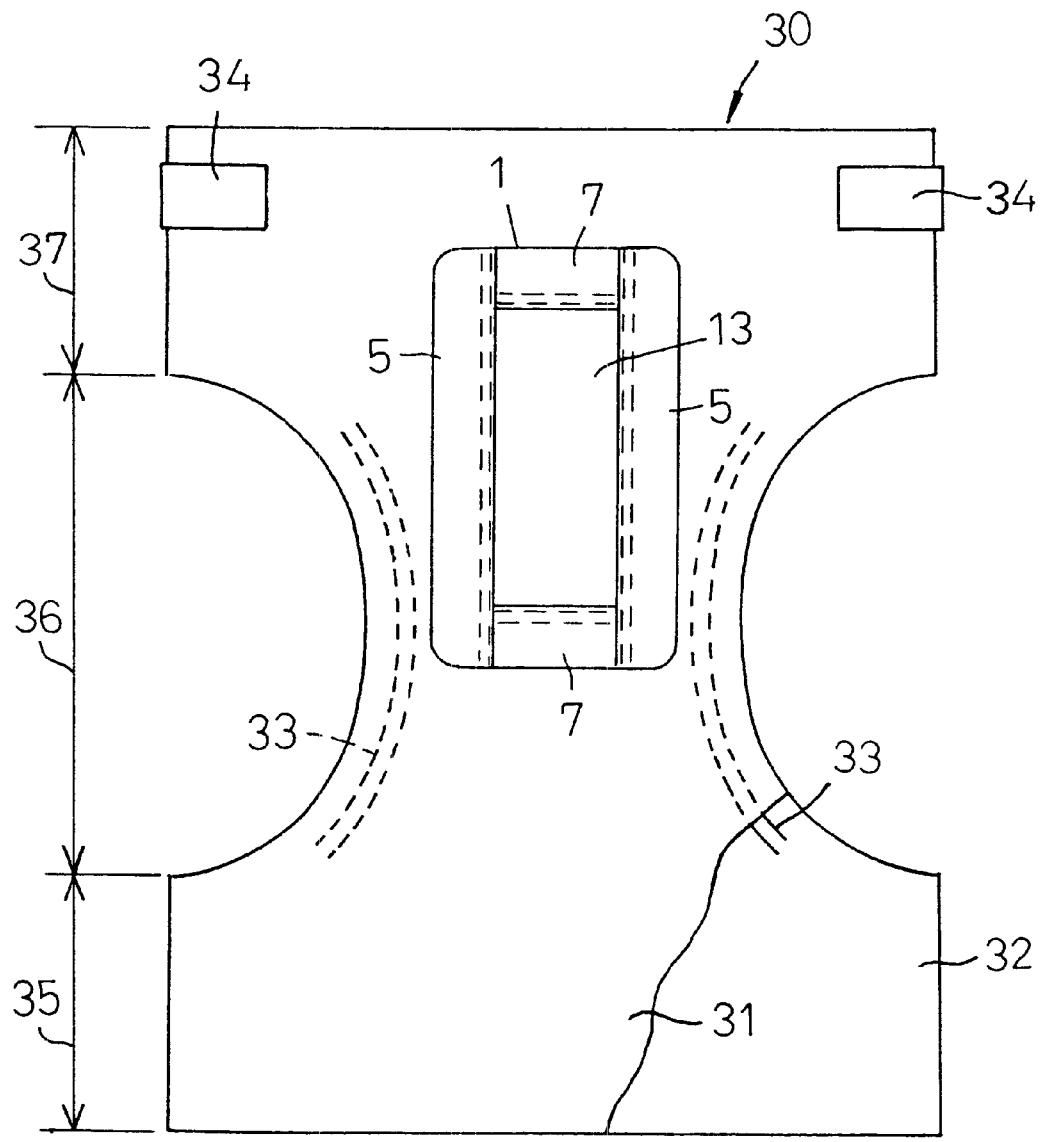
FIG. 5 is a plan view showing the article as attached to a diaper cover.

FIG. 5 is a plan view showing the panel 1 of FIG. 1 as attached to a diaper cover 30 as the cover 30 has been partially cutaway. The diaper cover 30 is an hourglass-shaped laminate consisting of an inner sheet 31 made of plastic film and an outer sheet made of nonwoven fabric. The cover 30 has longitudinally front and rear waist regions 35, 37 and a crotch region 36 extending between these front and rear waist regions 35, 37. Transversely opposite side edges of the crotch region 36 are curved inwardly of the cover 30.

The transversely opposite side edges of the crotch region 36 are provided with elastic members 33 longitudinally extending and secured under tension to the inner surface of at least one of the inner and outer sheets 31, 32. The panel 1 is detachably attached to the inner surface of the cover 30 by means of adhesive agent (not shown) so that the panel 1 may extend from the rear waist region 37 into the crotch region 36. The position at which the panel 1 is attached to the diaper cover 30 may be selectively shifted to use the assembly for the purpose of disposal of urine and menstrual discharge or for disposal of faces.

The cover 30 is provided on transversely opposite side edges of the rear waist region 37 with a pair of tape fasteners 34. As in the case of the conventional disposable diaper, these tape fasteners 34 enable the assembly of the panel 1 and the cover 30 to be put on a wearer's body so that the wearer's anus may be positioned substantially at a center of the panel opening 13.

With the panel 1 being used in this manner, excretion is discharged into the opening 13 and it is not concerned that the cover 30 might be soiled with excretion. Disposal of excretion can be easily done merely by holding the panel 1 substantially smaller than the cover 30.

The barrier side flap 5 and the barrier end flap 7 provided along the transversely opposite side edges 1a and the longitudinally opposite ends 1b of the panel 1, respectively, function as the barriers against leakage of body wastes. Accordingly, it is unnecessary to provide the transversely opposite side edges with a pair of barrier flaps elastically biased to rise on the upper surface of the cover 30.

The topsheet 2 may be made of a liquid-pervious sheet such as a nonwoven fabric or porous plastic film, preferably a liquid-pervious but hydrophobic sheet. The backsheet 3 may be made of a liquid-impervious plastic film, a laminate of plastic film and hydrophobic nonwoven fabric, or preferably a breathable liquid-impervious sheet.

The barrier side flap 5 and the barrier end flaps 7 may be made of a breathable liquid-impervious nonwoven fabric or breathable, liquid-impervious and elastic nonwoven fabric. If the elastic nonwoven fabric is used, the barrier side flap 5 may be joined with a longitudinal tension to the panel 1 while the barrier end flap 7 may be joined with a transverse tension to the panel 1 to eliminate use of the elastic members 6, 8 associated with the upper side sections 5a of the barrier side flaps 5 and the upper end sections 7a of the barrier end flaps 7, respectively.

The nonwoven fabric used as the stock material may be selected from a group including those of spun lace, needle punch, melt blown, thermal bond, spun bond and chemical bond types. A basis weight is 15~80 g/m$^2$, preferably 20~60 g/m$^2$. Component fiber may be selected from a group including polyolefine, polyester, polyamide fibers, and a conjugated fiber or polyethylene/polypropylene or polyester.

The core 4 is formed by compressing a mixture of fluff pulp and hydrogel particles of high water absorptivity and then covering it entirely with a water-pervious sheet such as tissue paper.

Bonding of these members 2, 3, 5, 7 and the elastic members 6, 8 may be achieved using adhesive agent such as hot melt adhesive, glue or heat-sealing technique.

This invention applicable also to the independent article for disposal of body wastes adapted to be directly attached to shorts or pants without being combined with the diaper cover 30.

The disposable body wastes absorbent article according to this invention is adapted for disposal of urine or fecal matter as well as for disposal of menstrual discharge by selectively shifting a position at which the article is attached to the cover member. The article according to this invention additionally enables the body wastes such as excretion or menstrual discharge to be reliably received through the opening into the article and then to be absorbed by the core through the topsheet.

The barrier side flap and the barrier end flaps are biased to move away from the upper surface of the panel and thereby to be smoothly risen on the upper surface of the panel. The upper sections of the respective barrier side flaps risen cooperates with the topsheet to form the pockets opening inwardly of the panel. The upper sections of the respective barrier end flaps risen cooperate with the topsheet to form the pockets opening inwardly of the panel. In this manner, the excretion discharged onto the panel is reliably prevented from leaking beyond its transversely opposite side edges regions and its longitudinally opposite ends.

What is claimed is:

1. A laminated panel for a disposable body wastes absorbent article having transversely opposite side edges and longitudinally opposite ends, said laminated panel comprising:

a liquid-pervious topsheet;

a liquid-impervious backsheet;

a liquid-absorbent core disposed between the liquid-pervious topsheet and the liquid-impervious backsheet;

a pair of barrier side flaps provided along said transversely opposite side edges of the disposable body wastes absorbent article and extending longitudinally of said laminated panel and being biased to rise above an upper surface of the laminated panel; and a pair of barrier end flaps provided along said longitudinally opposite ends of the disposable body wastes absorbent article and extending transversely of said laminated panel, each of said barrier side flaps comprises:

a first side section extending above an upper side of said laminated panel longitudinally thereof;

a second side section extending on a lower side of said laminated panel longitudinally thereof; and longitudinally opposite ends overlying said longitudinally opposite ends of said laminated panel on the upper side thereof, said second side section being folded in a sidewise U-shaped configuration along a folding line extending longitudinally of said lasted panel with an open end of said U-shaped configuration being opposed to said first side section and with an inner surface of said second side portion laid flat together so as to define a free side subsection and a fixed side subsection placed on said free side subsection and said fixed side subsection having an upper surface thereof fixed to the lower surface of said laminated panel along said transversely opposite side edges thereof, said folding line lying beneath and inward of side edges of the liquid-impervious backaheet;

each of said barrier end flaps comprises:

a first end section extending above the upper surface of said laminated panel transversely thereof;

a second end section extending on the lower surface of said laminated panel transversely thereof; and transversely opposite ends overlying said longitudinally opposite ends of said laminated panel on an upper side thereof, said second section being folded in a sidewise U-shaped configuration along a folding line extending transversely of said laminated panel with an open end of said U-shaped configuration being opposed to said first end section and with an inner surface of said second side section laid flat together so as to define a free end subsection and a fixed end subsection placed on said free end subsection, and said fixed end subsection having a upper surface thereof fixed to the lower surface of said laminated panel along said longitudinally opposite ends thereof, said folding line lying beneath and inward of end edges of the liquid-impervious backsheet, said longitudinally opposite ends of said barrier side flaps are collapsed inward transversely of said laminated panel while said transversely opposite ends of said barrier end flaps are collapsed inward longitudinally of the laminated panel to place said longitudinally opposite ends of said barrier side flaps and said transversely opposite ends of said barrier end flaps upon each other, said longitudinally opposite ends of said barrier side flaps being fixed to said transversely opposite ends of said barrier end flaps.

2. The article according to claim 1, wherein said barrier side flaps and said barrier end flaps are each formed from a nonwoven fabric, and said barrier side flaps are provided along said first side sections with at least one elastic member extending longitudinally of said laminated panel and secured under tension and said barrier end flaps are provided along said first end sections with at least one elastic member extending transversely of said laminated panel and secured under tension.

3. The article according to claim 1, wherein said barrier side flaps and said barrier end flaps are each formed from an elastic nonwoven fabric, said barrier side flaps are joined to said laminated panel under tension directed longitudinally of said laminated panel, and said barrier end flaps are joined to said laminated panel under tension directed transversely of said laminated panel.

4. The article according to claim 1, wherein flexible side flaps are formed from portions of said topsheet and said backsheet which portions extend outward from lateral side edges of said core, said fixed side subsections of said first side sections being fixed on a lower surface of said side flaps and said fixed end subsections of said first end sections being fixed on the lower surface of said side flaps.

5. The article according to claim 1, wherein said laminated panel comprises an absorbent pad that is attached to an inner surface of a diaper cover.

6. The article according to claim 1, wherein flexible side flaps are formed from portions of said topsheet and said backsheet which portions extend outward from lateral side edges of said flaps and said fixed end subsections of said first end sections being fixed on the lower surface of said side flaps.

7. The article according to claim 1, in combination with a diaper cover.

8. A laminated panel for a disposable body wastes absorbent article, said laminated panel comprising:
  a liquid-pervious topsheet;
  a liquid-impervious backsheet;
  a liquid-absorbent core disposed between the liquid-pervious topsheet and the liquid-impervious backsheet;
  a pair of barrier side flaps extending longitudinally of said laminated panel and being biased to rise above an upper surface of the laminated panel; and
  a pair of barrier end flaps extending transversely of said laminated panel, each of said barrier side flaps comprises:
  a first side section extending above an upper side of sad laminated panel longitudinally thereof;
  a second side section extending on a lower side of said laminated panel longitudinally thereof; and
  longitudinally opposite ends overlying said longitudinally opposite ends of said laminated panel on the upper side thereof, said second side section being folded in a sidewise U-shaped configuration along a folding line extending longitudinally of said laminated panel with an open end of said U-shaped configuration being opposed to said first side section and with an inner surface of said second side portion laid flat together so as to define a free side subsection and a fixed side subsection placed on said free side subsection and said fixed side subsection having an upper surface thereof fixed to the lower surface of said laminated panel along said transversely opposite side edges thereof, said folding line lying beneath and inward of side edges of the liquid-impervious backsheet;

each of said barrier end flaps comprises:
  a first end section extending above the upper surface of said laminated panel transversely thereof;
  a second end section extending on the lower surface of said laminated panel transversely thereof; and
  transversely opposite ends overlying said longitudinally opposite ends of said laminated panel on an upper side thereof, said second section being folded in a sidewise U-shaped configuration along a folding line extending transversely of said laminated panel with an open end of said U-shaped configuration being opposed to said first end section and with an inner surface of said second side section laid flat together so as to define a free end subsection and a fixed end subsection placed on said free end subsection, and said fixed end subsection having a upper surface thereof fixed to the lower surface of said laminated panel along said longitudinally opposite ends thereof, said folding line lying beneath and inward of end edges of the liquid-impervious backsheet, said longitudinally opposite ends of said barrier side flaps are collapsed inward transversely of said laminated panel white said transversely opposite ends of said barrier end flaps are collapsed inward longitudinally of the laminated panel to place said longitudinally opposite ends of said barrier side flaps and said transversely opposite ends of said barrier end flaps upon each other, said longitudinally opposite ends of said barrier side flaps being fixed to said transversely opposite ends of said barrier end flaps.

9. The article according to claim 8, wherein said barrier side flaps and said barrier end flaps are each formed from a nonwoven fabric, and said barrier side flaps are provided along said first side sections with at least one elastic member extending longitudinally of said laminated panel and secured under tension and said barrier end flaps are provided along said first end sections with at least one elastic member extending transversely of said laminated panel and secured under tension.

10. The article according to claim 8, wherein said barrier side flaps and said barrier end flaps are each formed from an elastic nonwoven fabric, said barrier side flaps are joined to said laminated panel under tension directed longitudinally of said laminated panel, and said barrier end flaps are joined to said laminated panel under tension directed transversely of said laminated panel.

* * * * *